US008715744B2

(12) United States Patent
Gerber

(10) Patent No.: US 8,715,744 B2
(45) Date of Patent: May 6, 2014

(54) INORGANIC RESORBABLE BONE SUBSTITUTE MATERIAL

(75) Inventor: Thomas Gerber, Sildemow (DE)

(73) Assignee: Artoss GmbH, Rostock (DE)

( * ) Notice: Subject to any disclaimer, the term of this patent is extended or adjusted under 35 U.S.C. 154(b) by 1273 days.

(21) Appl. No.: 10/557,796

(22) PCT Filed: May 24, 2004

(86) PCT No.: PCT/EP2004/005709
§ 371 (c)(1),
(2), (4) Date: Aug. 25, 2006

(87) PCT Pub. No.: WO2004/103421
PCT Pub. Date: Dec. 2, 2004

(65) Prior Publication Data
US 2007/0059379 A1    Mar. 15, 2007
US 2008/0152723 A9    Jun. 26, 2008

(30) Foreign Application Priority Data

May 22, 2003  (DE) .................................. 103 23 079
Aug. 22, 2003  (DE) .................................. 103 38 634

(51) Int. Cl.
*A61L 27/12* (2006.01)
(52) U.S. Cl.
USPC .......................................... 424/602; 977/906
(58) Field of Classification Search
None
See application file for complete search history.

(56) References Cited

U.S. PATENT DOCUMENTS

| | | | |
|---|---|---|---|
| 4,861,733 A | 8/1989 | White | |
| 5,133,756 A | 7/1992 | Bauer et al. | |
| 5,525,148 A | 6/1996 | Chow et al. | |
| 5,650,108 A | 7/1997 | Nies et al. | |
| 5,658,332 A | 8/1997 | Ducheyne et al. | |
| 5,981,412 A | 11/1999 | Hench et al. | |
| 5,997,624 A | 12/1999 | Chow et al. | |
| 6,054,400 A | 4/2000 | Brink et al. | |
| 6,183,515 B1* | 2/2001 | Barlow et al. | 623/16.11 |
| 6,537,589 B1* | 3/2003 | Chae et al. | 424/602 |
| 2003/0060536 A1 | 3/2003 | Spange et al. | |
| 2003/0152606 A1 | 8/2003 | Gerber | |

FOREIGN PATENT DOCUMENTS

| | | | |
|---|---|---|---|
| CA | 2 396 604 A1 | 1/2003 | |
| DE | 198 25 419 A1 | 12/1999 | |
| DE | 12825419 * | 12/1999 | C04B 38/00 |
| WO | WO 03/093196 A1 | 11/2003 | |

OTHER PUBLICATIONS

Falaize et al, 1999. In vitro behavior of silica-based xerogels intended as controlled release carriers. Journal of Ceramic Society, vol. 82(4):969-76.*
Santos et al, 1999. Sol-gel derived carrier for controlled release of proteins. Biomaterials, vol. 20:1695-1700.*
NIST, 1997. National Institute of Standards and Technology, Certificate of Analysis for Standard Reference Material 2910, Calcium Hydroxapatite.*
Gerber et al, 2002. A new sol-gel derived bone grafting material. Key engineering Materials, vol. 218-220:399-44.*
Gerber et al ("Development of Bioactive Sol-Gel Material Template for In Vitro and In Vivo Synthesis of Bone Material," Journal of Sol-Gel Science and Technology 19, 441-445, 2000).*
"New Bone?" *The Lancet*, 339:463-464 (1992).
Bruijn et al., "The Ultrastructure of the Bone-Hydroxyapatite Interface in vitro", *Jounral of Biomedical Materials Research*, 26:1365-1382 (1992).
Daculsi, "Biphasic Calcium Phosphate Concept Applied to Artificial Bone, Implant Coating and Injectable Bone Substitute", *Biomaterials*, 19:1473-1478 (1998).
Kenley et al., "Biotechnology and Bone Graft Substitutes", *Pharmaceutical Research*, 10:1393-1401 (1993).
Klein et al., "Studies of the Solubility of Different Calcium Phosphate Ceramic Particles in vitro", *Biomaterials*, 11:509-512 (1990).
Knabe et al., "Morphological Evaluation of Osteoblasts Cultured on Different Calcim Phosphate Ceramics", *Biomaterials* 18(20):1339-1347 (1997).
Lazić, "Microcrystalline Hydroxyapatite Formation from Alkaline Solutions", *Journal of Crystal Growth*, 147:147-154 (1995).
Lundager Madsen, "Precipitation of Calcium Phosphate from Moderately Acid Solution", *Journal of Crystal Growth*, 66:369-376 (1984).
Nagano, "Growth of $SnO_2$ Whiskers by VLS Mechanism", *Journal of Crystal Growth*, 66:377-379 (1984).
Oonishi et al., "Comparative Bone Growth Behavior in Granules of Bioceramic Materials of Various Sizes", *J. Biomed. Mater. Res.* 44::31-43 (1999).
Osborn et al., "The Material Science of Calcium Phosphate Ceramics", *Biomaterials*, 1:108-111 (1980).
Pollick et al., "Bone Formation and Implant Degradation of Coralline Porous Ceramics Placed in Bone and Ectopic Sites", *J. Oral Maxillofac Surg.*, 53:915-922 (1995).
Sun et al., "The Effects of Calcium Phosphate Particles on the Growth of Osteoblasts", *J. Biomed. Mater. Res.* 37:324-334.
Vuola et al., "Compressive Strength of Calcium Carbonate and Hydroxyapatite Implants After Bone-Bone-Marrow-Induced Osteogenesis", *Biomaterials*, 19:223-227 (1998).
Yuan et al., "A Preliminary Study on Osteoinduction of Two kinds of Calcium Phosphate Ceramics", *Biomaterials* 20:1799-1806 (1999).
Gerber et al., "Nanostructuring of Biomaterials—A Pathway to Bone Grafting Substitute", *Eur J Trauma* 32:132-140 (2006).
Dorozhkin, "Nanodimensional and Nanocrystalline Apatites and Other Calcium Orthophosphates in Biomedical Engineering, Biology and Medicine," *Materials*, 2:1975-2045 (2009).

(Continued)

*Primary Examiner* — Suzanne Ziska
(74) *Attorney, Agent, or Firm* — Arnold & Porter LLP

(57) ABSTRACT

The invention relates in particular to a hydroxyl apatite/silica granular material of defined morphology, a highly porous bone substitute material based on this granular material and a glass ceramic material based in turn thereon as bone substitute material which is characterized by a variable mechanical strength, and shaped bodies of this material, materials of different mechanical strength being preferably used in the shaped body. The bone substitute materials according to the invention are characterized by a high resorbability in vivo.

49 Claims, 6 Drawing Sheets

(56) References Cited

OTHER PUBLICATIONS

Murugan et al., "Development of nanocomposites for bone grafting," *Composites Science and Technology*, 65:2385-2406 (2005).
Berkeley Advanced Biomaterials, Inc. catalog (available at www.hydroxyapatite.com/), 5 pp. (Jun. 2010).
Best et al., "The Dependence of Osteoblastic Response on Variations in the Chemical Composition and Physical Properties of Hydroxyapatite," *Journal of Materials Science: Materials in Medicine*, 8:97-103 (1997).
McDowell et al., "Solubility of $Ca_5(PO_4)_3OH$ in the system $CA(OH)_2$-$H_3PO_4$-$H_2O$ at 5, 15, 25, and 37° C," *Journal of Research of the National Bureau of Standards—A. Physics and Chemistry*, 81A(2 and 3):273-281 (1977).
Nakano et al., "Variation in Crystallinity of Hydroxyapatite and the Related Calcium Phosphates by Mechanical Grinding and Subsequent Heat Treatment," *Metallurgical and Materials Transactions A*, 33A:521-528 (2002).
Rossi et al., "Structural Properties of Hydroxyapatite with Particle Size Less than 10 Nanometers," *Key Engineering Materials*, 330-332:255-258 (2007).

\* cited by examiner

INORGANIC RESORBABLE BONE SUBSTITUTE MATERIAL

CROSS-REFERENCE TO RELATED APPLICATIONS

This national phase application is a continuation application of International Application No. PCT/EP2004/005709, filed May 24, 2004, which claims priority to German Patent Application Nos. 103 23 079.3, filed May 22, 2003, and 103 38 634.3, filed Aug. 22, 2003. The disclosures of these applications are hereby incorporated by reference in their entirety.

The invention relates in particular to a granular hydroxyl apatite/silica material of defined morphology, a highly porous bone substitute material based on this granular material and a glass ceramic material based thereon in turn as bone substitute material which is characterised by a variable mechanical strength, and shaped bodies of this material, materials of different mechanical strength being preferably used in the shaped body. The bone substitute materials according to the invention are characterised by a high resorbability in vivo.

Bone grafts are the second most frequent type of transplant in humans, second only to the administration of blood components (Fox, R: New bone, The Lancet 339, 463 ff (1992)). Thus, 250,000 bone grafts were carried out in the USA in 1993 (Kenley et al: Biotechnology and bone graft substitutes. Pharmaceut. Res. 10, 1393 (1993)). The replacement of congenital, post-traumatic and osteoporotic bone defects occurring as a result of osteomyelitides and tumour operations is of the utmost clinical significance since a functionally comprehensive rehabilitation is possible only in this way.

In the literature, numerous porous materials are described as bone substitutes. In 1992, a ceramic material produced from cattle bone was published, the entire organic matrix being removed and the ceramic portion being annealed at temperatures of 1100° C. to 1500° C. (Bauer G, Vizethum, F., Process for producing a bone substitute material. U.S. Pat. No. 5,133,756; 1992).

Some processes for the production of porous bone substitute substances make use of the skeleton of natural corals (Pollick S, Shors, E C, Holmes R E, Kraut R A. Bone formation and implant degradation of coralline porous ceramics placed in bone and ectopic sites. J. Oral Maxillofac Surg 1995; 53 (8): 915-23, White, E W. Calcium phosphate bone substitute materials. U.S. Pat. No. 4,861,733; 1989) which exhibit an ideal pore structure (size distribution, morphology) for the ingrowth of the bone tissue.

The decisive disadvantage of these ceramic materials is that they are not resorbable (Jenssen S S, Aaboe M, Pinholt E M, Hjorting-Hansen E, Melsen F, Ruyter I E. Tissue reaction and material characteristics of four bone substitutes. Int J Oral Maxillofac Implants. 1996; 11 (1): 55-66). The bone formed is subject to continual restructuring, also called remodelling, osteoclasts degrading the bone and osteoblasts rebuilding it. For the materials described, this means that the bone tissue grows excellently into the pore structure while the highly crystalline hydroxyl apatite of the ceramic material, however, no longer participates in bone remodelling. For this reason, it remains a foreign body and unfavourably influences the mechanical properties of the bone regenerate. In addition, an inflammation reaction occurs in the interface area between the tissue and the ceramic material (Gunther K P, Scharf H-P, Pesch H-J, Puhl W. Einwachsverhalten von Knochenersatzstoffen (Ingrowth behaviour of bone substitute materials) Orthopädie 1998; 27: 105-117, Sailer J D, Weber F R. Knochenersatzmaterialien (Bone substitute materials) Mund Kiefer Gesichts Chir 2000; 4 (Suppl. 1) 384-391).

Porous materials based on hydroxyl apatite (HA) are an ideal bone substitute since they promote tissue regeneration as a result of a special surface characteristic. However, in the literature, it is generally stated that these ceramic materials do not have an osteoinductive effect in the actual sense (Heymann D, Delecrin J, Deschamps C, Gouin, F Padrines M, Passuti N. In vitro assessment of associating osteogenic cells with macroporous calcium-phosphate ceramics. Rev Chir Orthop Reparatrice Appar Mot 2001; 87 (1): 8-17, Osborne J F, Newesely H. The material science of calcium phosphate ceramics. Biomaterials 1980; 1: 108-112, Vuola J, Taurio R, Goransson H, Asko-Seljavaara S. Compressive strength of calcium carbonate and hydroxy apatite implants after bone-marrow-induced osteogenesis. Biomaterials 1998; 19 (1-3): 223-7). Instead, close fitting bonding to the bone takes place as a result of protein adsorption and the addition of osteoblasts to a primary biological apatite layer covering the implant (De Bruijn J D, Klein C P A T, De Groot K, Van Blitterswijk C A. Ultrastructure of the bone-hydroxyl apatite interface in vitro. J Biomed Mater Res. 1992; 26: 1365-1382, Donath K, Hormann, K, Kirsch A. Welchen Einfluss hat Hydroxylapatitkeramik auf die Knochenbildung? (Which influence does the hydroxyl apatite ceramic material have on bone formation?) Dtsch Z Mund Kiefer Gesichtschir. 1985; 9 (6): 438-40).

Yuan et al., on the other hand (Yuan H, Kurashina K, de Bruijn J D, Li Y, de Groot K, Zhang X. A preliminary study on osteoinduction of two kinds of calcium phosphate ceramics. Biomaterials 1999; 20 (19): 1799-806) has found that it is possible to induce osteoinductive properties as a function of the microstructure of the ceramic material with an identical chemical and crystallographic structure of the calcium phosphate.

This means that these materials are capable of inducing a dystopic bone formation, for example when they are implanted under the skin or into the muscle tissue where no other osteoinductive stimuli are present. These osteoinductive properties (bone formation in extraosseal sites) is also caused in various hydroxyl apatite ceramics (HA ceramics) if they have been saturated with bone marrow cells (Heymann D, Delecrin J, Deschamps C, Gouin F Padrines M, Passuti N. In vitro assessment of associating osteogenic cells with macroporous calcium-phosphate ceramics. Rev Chir Orthop Reparatrice Appar Mot 2001; 87 (1): 8-17, Vuola J, Taurio R, Goransson H, Asko-Seljavaara S. Compressive strength of calcium carbonate and hydroxy apatite implants after bone-marrow-induced osteogenesis. Biomaterials 1998; 19 (1-3): 223-7).

Dagulsi describes the cell reaction, biodegradation and bioresorption as well as the transformation to carbonate hydroxyl apatite of a two-phase material (HA/TCP) which has been used as shaped body, coating as well as injectable bone substitute material (Dagulsi G. Biphasic calcium phosphate concept applied to artificial bone, implant coating and injectable bone substitute. 1998, 19 (16): 1473-8).

Within the framework of the development of a resorbable bone substitute substance, the influence of different calcium phosphates and combinations of calcium phosphates on the development of osteoblasts was examined in vitro. In a comparative study, Oonishi et al implanted different bioceramic materials into the condyle of the femur of adult Japanese white rabbits and indicate the following resorption activities as being the result: HA with a low degree of crystallinity, OCP>TeCP, TeDCPD, TeDCPA>αTCP, βTCP (Oonishi H, Hench L L, Wilson J, Sugihara F, Tsuji E, Kushitani S, Iwaki H. Comparative bone growth behaviour in granules of bioceramic materials of various sizes. J Biomed Mater Res 1999: 44 (1): 31-43).

Sun et al found that a combination of hydroxyl apatite and β-tricalcium phosphate (βTCP) has an inhibiting effect on the growth of the osteoblasts. The effect of calcium phosphate particles on the growth of osteoblasts (Sun J S, Tsuang Y H, Liao C J, Lui, H C, Hang, F K. The effects of calcium phosphate particles on the growth of osteoblasts. J Biomed Mater Res 1997; 37 (3): 324-334).

The influence of different resorbable ceramics such as e.g. $CaNaPO_4$, $CaNaPO_4+MgNaPO_4$, $CaNaPO_4+Mg_2SiO_4$, among others, on the growth of the osteoblasts was investigated in vitro (Knabe C, Gildenhaar R, Berger G, Ostapowicz W, Fitzner R, Radlanski R J, Gross U. Morphological evaluation of osteoblasts cultured on different calcium phosphate ceramics. Biomaterials 1997; 18 (20): 1339-1347). The best support for the growth of osteoblasts was found with $CaNaPO_4+MgNaPO_4$ and $Ca_2KNa(PO_4)_2$. If too many $Ca^{2+}$ ions are released by the ceramic material, cell growth is inhibited.

In a study of the condyles of the femur of fully grown rabbits, Oonishi et al compare the ingrowth behaviour of granules of a bioglass and synthetic temperature-treated hydroxyl apatite (Oonishi H, Hench L L, Wilson J, Sugihara F, Tsuji E, Matsuura M, Kin S, Yamamoto T, Mizokawa S. Quantitative comparison of bone growth behaviour in granules of bioglass, A-W glass-ceramic, and hydroxy apatite. J Biomed Mater Res 2000; 51 (1): 37-46). In contrast to bioglass, synthetic hydroxyl apatite is not completely resorbed.

Bioactive types of glass are also described as bone substitute material (U.S. Pat. No. 6,054,400; 2000; U.S. Pat. No. 5,658,332; 1997). In this case, the inorganic material is present as a glassy solid. Pores of the order of magnitude of the spongy bone allow an ingrowth of the tissue. Smaller pores are not present in the material.

Glass ceramics, too, are offered as bone substitute (e.g. U.S. Pat. No. 5,981,412; 1999). They can be compared to the bioactive types of glass, a crystalline component such as e.g. $Na_2O\ 2CaO.3SiO_2$ being incorporated into the glass matrix which, in general, is a bioactive calcium silicate glass.

As a further substance group for use a bone substitute, calcium phosphate cements have been developed (U.S. Pat. No. 5,997,624; 1999; U.S. Pat. No. 5,525,148; 1996). A decisive disadvantage of this group of substances is that no defined interconnecting pores are introduced into the material as a result of which they are restricted to very small bone defects.

In the patents DE 198 25 419 and DE 100 03 824, processes have been described by means of which highly porous calcium phosphate ceramic materials based on hydroxyl apatite can be produced by means of the sol-gel technique, which are intended specifically for filling and the reconstruction of bone defects of different size. The processes aim at producing highly porous structures. Using the process of patent DE 198 25 419, a porosity of up to 70% is achieved, the pores being in the range of 1-10 micrometers. In patent DE 100 03 824, a process is described which, additionally, produces a pore structure of the order of magnitude of 0.1 to approximately 1 millimeter, such as that which is present also in natural spongiosa.

In DE 100 60 036, an inorganic resorbable bone substitute material is described which possesses a loose crystal structure, i.e. the crystallites are not tightly joined as in a solid body (ceramic material) but connected only via some groups of molecules. The volume which, in the natural bone, is taken up by collagen, is present in the material as interconnecting pores in the nanometer region. A second pore size, which is also interconnecting and in the region of a few micrometers, permits an ingrowth of collagen fibres during tissue formation. These fibres are nucleators for the starting biomineralisation (formation of the body-inherent biological apatite). The material contains a third interconnecting pore category which imitates the spongiosa, is in the region of approximately 100 μm to 1000 μm and consequently allows ingrowth of blood vessels as a result of which resorption and renewed bone formation occurs not only as a front of healthy bone but also out of the entire defect.

In the case of this material, the promotion of osteogenesis and the resorption property is in the foreground so that remodelling of the bone is supported.

In the relevant specialist literature, it is pointed out that bone substitute materials based on hydroxyl apatite are practically not resorbed and permanently represent a foreign body. In contrast to this, the material described in DE 100 60 036 which consists essentially of hydroxyl apatite is highly satisfactorily resorbed and, simultaneously, accelerates the renewed formation of bone tissue. This property is determined by the loose crystal structure of calcium phosphates described.

The mechanical strength of this material, however, is relatively low. It cannot exercise any mechanical support function. In addition, the possibilities of varying the bone substitute material in order to be able to use it for replacing entire bone fragments (e.g. parts of a tubular bone) are very limited.

In reconstructive surgery and in orthopaedic surgery, bone substitute materials which contain components with a higher mechanical strength are required in particular for relatively large defects. In connection with computer tomography on the patient and computer-supported production, substitute parts of the cranial bone, for example, can be formed as an imitation.

In contrast, the present invention is based on the task of providing a bone substitute which promotes a formation of bone tissue (which is thus osteoconductive and/or osteoinductive) which is resorbed via the natural processes of bone remodelling and possesses a mechanical strength which can correspondingly be adapted to the different applications. Defects in the bone, which may arise e.g. as a result of inflammation, are usually surrounded on several sides by healthy bone. For these defects, the mechanical strength of the bone substitute material is insignificant. If, however, entire bone segments are missing as a result of a comminuted fracture or the removal of a bone tumour, the bone substitute material must exert a supporting function. In this case, a substitute bone is made from the bone substitute material (e.g. a hollow cylinder for a missing piece of tubular bone) which is then screwed with osteosynthesis plates (metal plates which are removed after healing) to the remaining bone. The support function is now assumed by the system of substitute bone of bone substitute material and the osteosynthesis plate. Since it is certain that an increased mechanical strength leads to a reduced resorption, a compromise needs to be made regarding the material properties, depending on the size of the defect and the mechanical stress.

Figure 1:
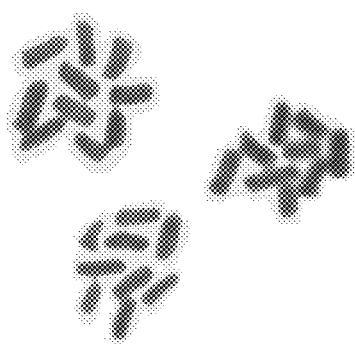
FIGS. 1 to 3 show materials according to an aspect of the present disclosure.

To solve the task, granular materials, highly porous bone substitute materials based on these granular materials, glass ceramic materials based thereon as bone substitute materials with a variable mechanical strength, uses, means, shaped bodies, processes etc. are proposed. For solution purposes, the products and the use of the attached claims are proposed.

According to the invention, the task is thus achieved by way of a material which contains crystalline calcium phosphate embedded in a xerogel matrix. This xerogel matrix consists of silica.

Xerogel is a dry gel which is characterised by a large internal surface area and incomplete crosslinking of the structural groups.

In this way a completely new type of material is available which is comparable with a glass ceramic material, the matrix containing the crystalline components not being glass in this case but a xerogel with its typical porous structure. The xerogel matrix should preferably occupy a proportion by weight of 4 to 80%, based on the total mass of the bone substitute material. Since a silica xerogel is a porous material in which $SiO_4/2$ tetrahedra are loosely joined and which has a large internal surface area with —SiOH groups, it is possible to build a matrix even with low proportions by weight, as a function of the size of the crystallites of the calcium phosphate, which matrix encloses the crystalline components. A reduction of the proportion of the matrix to less than 5% by weight is possible as a function of the size of the crystallites.

The xerogel matrix has different tasks. On the one hand, it obviously binds the crystalline components of the material together. The mechanical strength of the material is limited by the relatively loose joining of the silica. The fracture strength is typically in the region of 2 to 15 MPa (compare example 6). On the other hand, the porosity of the xerogel allows the resorption of the biomaterial and improves the bioactivity which is obviously produced above all by the calcium phosphate components by body-inherent proteins from the blood of the patient attaching themselves to the high internal surface. Consequently, the cells do not classify the biomaterial as foreign to the body.

Consequently, the subject matter of the invention is a granular material and a group of bone substitute materials based thereon which will be described below. The granular material is based on calcium phosphate in which crystalline calcium phosphate is embedded in a silica xerogel matrix, the crystallites having an average diameter of approximately 10 nm to approximately 2000 nm, preferably of 10 nm to 200 nm, wherein platelet-type crystallites with a thickness of 2.5 nm to 10 nm and an average diameter of 10 nm to 200 nm are particularly preferably contained therein. The granule grains exhibit an average diameter of approximately 1 µm to approximately 1000 µm, and the proportion of silica is in the region of approximately 2 to approximately 80% by weight, preferably in the region of approximately 4 to approximately 50% by weight.

The pores in the xerogel exhibit an average diameter in the region of 0.5 nm to 20 nm. They represent approximately 10% by volume to approximately 60% by volume, based on the volume of the granule grain, in the granule grains.

Preferably, the calcium phosphate is hydroxyl apatite.

In a particular embodiment, the granular material can, moreover, comprise soluble calcium phosphate, the soluble calcium phosphate being preferably present in a proportion of approximately 5% by weight to 50% by weight, based on the proportion of calcium phosphate. The soluble calcium phosphate is β-tricalcium phosphate (βTCP), in particular.

The xerogel of the granular material can, moreover, comprise one or several network modifier oxides. The network modifier oxide(s) is/are preferably present in a proportion of approximately 0.5 to approximately 35 mole %, preferably in a proportion of approximately 17 mole % to approximately 30 mole %, based on silica. The network modifier is in particular $Na_2O$.

In FIG. 1, a granule particle according to the invention is represented diagrammatically as an example. The crystallites (shown in black) in the granular material are held together by the $SiO_2$ xerogel (shown in grey). At the surface of the granule particles, $SiO_2$ xerogel is present.

It should be briefly noted that a granule grain from the preferred range of magnitude with a diameter of e.g. 1 µm contains crystallites of the order of magnitude of $10^4$ if these are e.g. platelets with a diameter of 100 nm and thickness of 10 nm and the xerogel matrix takes up 40% by weight of the granule grain.

On the basis of the granular hydroxyl apatite/silica material described, a highly porous bone substitute material as well as a glass ceramic material are obtained as bone substitute material with variable mechanical strength.

The starting point is a highly porous bone substitute material which is characterised in that the granule grains are bound together via the xerogel matrix and as a result of the packing of the granule grains, pores are formed which are of the order of magnitude of the granule grains. The highly porous bone substitute material consequently has two categories of pores.

Apart from the pores just described which are formed by the packing of the granule grains and are consequently in the micrometer region, the pores which are within the granular material and which have been described above are also present. These are the pores in the xerogel which exhibit an average diameter in the region of 0.5 nm to 20 nm.

Consequently, a porosity of preferably approximately 30% by volume to approximately 80% by volume is present in the highly porous bone substitute material.

Figure 2:
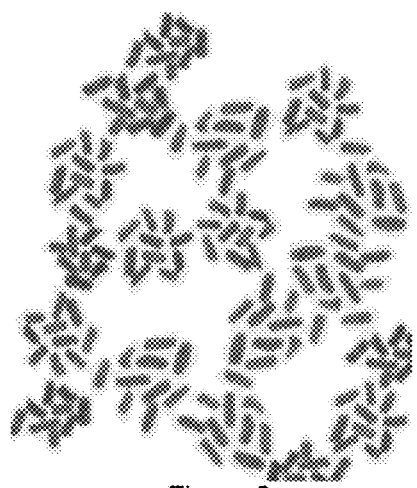

In FIG. 2, the structure of the highly porous bone substitute material is shown diagrammatically. An essential difference in comparison with bone substitute material of the state of the art consists in that the interior of the granule particles (i.e. the crystallites) is held together in a defined manner by $SiO_2$. The structure can be described in such a way that every individual crystallite is present in a xerogel matrix. The product can be obtained by partly conventional ceramic manufacturing processes when using the granular material described, as will be described in further detail below.

Moreover, the invention relates to a highly porous bone substitute material which comprises granule grains of the above-mentioned granular material which form a 3-dimensional structure which, apart from the pores present in the granule grains, also exhibits pores of approximately the size of the granule grains. Consequently, the pore diameter is in the region of approximately 1 µm to approximately 1000 µm, preferably in the region of approximately 1 µm to approximately 50 µm.

Small pieces (e.g. shaped bodies, particles, parts) of this highly porous bone substitute material, preferably in the form of cylinders with an average diameter of approximately 0.4 to approximately 2 mm and a length of approximately 1 to approximately 6 mm are used to fill small bone defects, preferably up to a size of 10 cm$^3$, in particular if the defects are surrounded on two sides by healthy bone.

Consequently, the invention also relates to a highly porous bone substitute material which is characterised in that it exhibits, moreover (i.e. additionally to the pores within the individual granule grains and additionally to the pores which are formed by the (3-dimensional) granule grain packing) interconnecting macropores in the region of approximately 100 µm up to several 1000 µm which have a volume proportion of approximately 10 vol % to approximately 60 vol %. Consequently, the highly porous bone substitute material preferably has an overall porosity of approximately 30 vol % to approximately 90 vol %, particularly preferably an overall porosity of approximately 60 vol % to approximately 80 vol %.

The fracture strength of the highly porous bone substitute material without the macropores described amounts to approximately 2 MPa to approximately 15 MPa, preferably approximately 3 to approximately 10 MPa. As a result of the macropores, the fracture strength of the material decreases and reaches values of only 0.1 MPa to 4 MPa.

According to a particularly preferred embodiment, the highly porous bone substitute material also contains one or several network modifier oxides. The network modifier oxide(s) is/are preferably present in a proportion of approximately 0.5 to approximately 35 mole %, preferably in a proportion of approximately 17 to approximately 30 mole %, based on the silica. Na$_2$O is particularly preferred.

Moreover, the invention relates to a glass ceramic material as bone substitute material (or —expressed differently, a bone substitute material comprising a glass matrix) which is characterised in that crystalline calcium phosphate is embedded into a glass matrix, the crystallites exhibiting a size of approximately 10 nm to approximately 2000 nm and the proportion of glass being in the region of approximately 4 to approximately 80% by weight (based on the total mass of the material), preferably in the region of approximately 2 to approximately 50% by weight, the glass containing silica as network modifier. Like the highly porous bone substitute material, the bone substitute material can also comprise one or several network modifiers. To avoid repetitions, reference is made with respect to the network modifier oxides to the full extent to the corresponding details provided above which apply equally to the bone substitute material described here.

The glass ceramic material according to the invention as bone substitute material is obtainable from an above-mentioned highly porous bone substitute material by converting the silica xerogel matrix with the network modifier, preferably sodium oxide, into the glassy state.

By way of this modification process, the nanoporous xerogel turns into a completely linked glass network which, having a fracture strength of approximately 300 MPa to approximately 400 MPa, increases the mechanical stability of the bone substitute material. The fracture strength of the bone substitute material described is dependent on the residual porosity described below such that the theoretical values are not achieved.

Consequently, the invention relates also to a bone substitute material in the case of which the glass matrix consists of sodium silicate. Preferably, it has a mechanical strength in the region of approximately 30 MPa to approximately 200 MPa, preferably approximately 50 MPa to approximately 120 MPa and exhibits a residual porosity of approximately 5 to approximately 35%, the pores having a diameter in the region of approximately 1 µm to approximately 200 µm.

Figure 3:
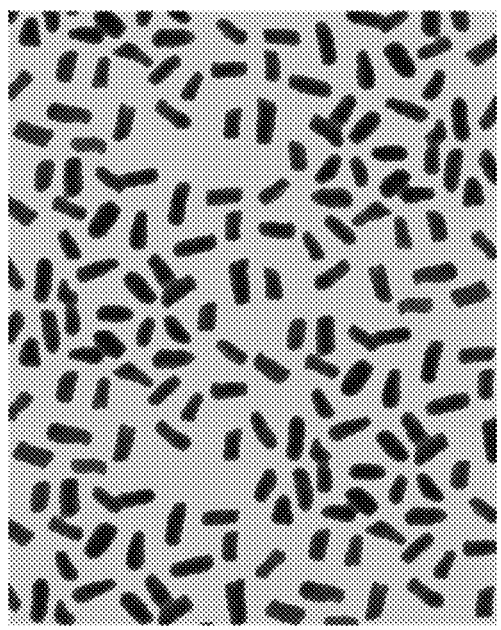

FIG. 3 shows the structure of the glass ceramic material diagrammatically. The calcium phosphate crystallites drawn in black have an identical structure to highly porous bone substitute material; however, they are now present in a glass matrix which is shown in grey. The residual porosity has not been represented in the diagrammatic representation.

The process of converting gel into glass is associated with sintering of the highly porous bone substitute material. The nanoporosity is completely eliminated and the described porosity in the micrometer region is reduced such that a residual porosity of approximately 2 to approximately 35 vol % is retained.

As a result of the described proportion of calcium phosphate in the glass matrix, the material is biocompatible. The process of resorption, however, has changed completely since no nanoporosity has remained.

Since the glass matrix preferably consists of sodium silicate glass, the sodium ions are dissolved slowly when the glass ceramic material is used as bone substitute material and the glass is converted into a gel-type structure with nanopores. The residual porosity in the micrometer region increases this effect. As a result of this process, a resorption of this bone substitute material is possible in the end.

Insofar as the process of the transition of the xerogel matrix of the highly porous bone substitute material described into the glass matrix takes place only partially, a bone substitute material can be obtained which can be adjusted regarding the mechanical properties and the resorption properties continually between the two extremes, namely the highly porous bone substitute material and the glass ceramic material as bone substitute material.

(Consequently), the invention relates to a bone substitute material which is characterised in that crystalline calcium phosphate is embedded into a matrix, the crystallites having a size of approximately 10 nm to approximately 2000 nm, the matrix consisting of a xerogel and of a glass, the proportion of glass of the matrix being between 0 and 100 vol %, preferably approximately 10 vol % to approximately 80 vol % and particularly preferably between approximately 60 vol % and approximately 80 vol %, xerogel and glass consisting of silica and a network modifier, preferably in a proportion of approximately 0.5 to approximately 35 vol %, preferably in a proportion of approximately 17 vol % to approximately 30 vol %, based on the silica, the network modifier preferably being sodium oxide and the matrix being in the region of approximately 2 to approximately 80% by weight, preferably in the region of approximately 4 to approximately 50% by weight of the bone substitute material.

The partial transition from xerogel to glass is achievable by heat treatment. Since the glass temperature of sodium silicate glass is in the region of approximately 460° C. to approximately 800° C., depending on the sodium content, it is clear that a heat treatment at above this temperature range leads very rapidly to glass. It a temperature treatment is carried out approximately 20% to approximately 5% below the glass temperature determined for the composition, the process is slowed down and requires several hours and can be broken off at any time.

A second possibility of carrying out the transition of xerogel to glass only partially consists of the use of two granular calcium phosphate/silica materials described above which differ by their proportion of network modifier. Preferably, a granular material without network modifier ($Na_2O$) and a granular material with approximately 20 mol % $Na_2O$, based on the xerogel, are selected. The highly porous bone substitute material is produced from these granular materials according to the process described below. If, subsequently, a heat treatment at approximately 520° C. is carried out, the areas with the $Na_2O$ are converted into the glassy state, the areas without any $Na_2O$ remain in the state of the xerogel since temperatures of approximately 1000° C. are required here.

According to a particular embodiment, the bone substitute material is a shaped body, in particular a cube, a plate, a hollow cylinder or a wedge.

Consequently, the subject matter of the invention is also a shaped body of the highly porous bone substitute material described which, on at least one side, comprises a layer of a bone substitute material mentioned above with a higher mechanical strength, preferably the glass ceramic material described, holes with a diameter if approximately 0.5 to approximately 5 mm being contained in this layer which holes exhibit a proportion by volume of approximately 5 to approximately 80%, based on the total volume of the layer, and these holes in turn being filled with the above-mentioned granular material and/or with the above-mentioned highly porous bone substitute material.

In the case of processes for the production of the materials described above which are, moreover, a subject matter of the invention, the starting point is the production of a granular calcium phosphate material which is characterised in that the crystallites are present in a xerogel matrix as described. Starting out from this granular material, the highly porous bone substitute material is produced which, in turn is a precondition for the production of the glass ceramic material as bone substitute material.

According to the invention, the production of the calcium phosphate is combined with a gel formation process of the silica during the production of the silica-containing granular material, via a precipitation reaction during which a so-called slip is formed. Only in this way can separate nanocrystallites be incorporated into a xerogel matrix. The granular silica-containing calcium phosphate materials are preferably hydroxyl apatite/silica granular material comprising optionally also soluble calcium phosphate.

In general, the synthesis for the production of calcium phosphates and also in particular of hydroxyl apatite takes place in an aqueous solution (C. P. A. T Klein, J. M. A. De Blieck-Hogerworst, J. G. C. Wolke, K. De Groot, Biomaterials, 11, 509 (1190)). The hydroxyl apatite synthesis can take place in an alkaline medium and provides thermally stable pure phase crystallites (M. Asada, Y. Miura, A. Osaka, K. Oukami, S. Nakamura, J. Mat. Sci. 23, 3202 (1988); S. Lazic, J. Cryst. Growth, 147, 147 (1995)). The hydroxyl apatite synthesis in a neutral or slightly acidic environment is also possible but more difficult to control (H. E. L. Madsen, G. Thodvadarson, J. Cryst. Growth, 66, 369 (1984)).

The starting point is e.g. calcium nitrate and ammonium hydrophosphate with a ratio of calcium to phosphate of 10:6 if hydroxyl apatite is to be obtained (U.S. Pat. No. 5,858,318). Other starting materials are $NaHCO_3$ and $CaHPO_4$ (Th. Leventouri, H. Y. Moghaddam, N. Papanearchou, C. E. Bunaciu, R. L. Levinson, O. Martinez, Mat. Res. Soc. Symp. Proc. 599, 79 (2000)) or $Ca(H_2PO_4)$ and $CaCl_2$ (M. Okido, R. Ichina, K. Kuroda, R. Ohsawa, O. Takai, Mat. Res. Soc. Symp. Proc. 599, 153 (2000)). Here, too, a ratio of calcium to phosphorus of 1.67 is chosen when hydroxyl apatite is to be obtained.

It is also possible to carry out the precipitation reaction with lime milk and phosphoric acid (DE 42, 32 443 C1, U.S. Pat. No. 4,274,879). If hydroxyl apatite, for example, is produced via these starting materials, which can in turn be controlled by the ratio of calcium to phosphorus of the starting products, dicalcium phosphate is frequently formed as by-product, which is undesirable. It is also advantageous to start out from pure soluble starting products and not to use lime milk (a dispersion).

In the quoted literature it is described how the parameters of pH, homogeneity of the mixture of the starting products and temperature influence the size of the crystallites and the degree of crystallinity of the end products. The connection between the pH and the temperature of the solution, in particular, is important (M. Okido, R. Ichina, K. Kuroda, R. Ohsawa, O. Takai, Mat. Res. Soc. Symp. Proc. 599, 153 (2000)). It is remarkable that hydroxyl apatite precipitates out in almost all solutions in a finely crystalline manner, i.e. as nanocrystallites and that, for certain applications e.g. as cleaning body in dental care, there is a search under way for process steps leading instead to larger crystallites (DE 43 32 443 C1).

The quantities of the starting products are selected in such a way that a ratio of Ca/P of 1.50 to 1.67 arises. The precipitation product in this range is always a so-called "precipitated hydroxy apatite" (PHA, $Ca_{10-x}(HPO_4)_x(PO_4)_{6-x}(OH)_{2-x}$). In the course of further treatment which includes also temperature treatments, hydroxyl apatite is formed completely from the "precipitated hydroxy apatite" at temperatures above approximately 650° C. if the ratio of calcium to phosphate (ratio of Ca/P) is precisely 1.67. With a ratio of Ca/P of 1.5, almost the entire hydroxyl apatite is converted into β-tricalcium phosphate. By way of a Ca/P ratio of between 1.5 and 1.67, a mixture of β-tricalcium phosphate and hydroxyl apatite is obtained whose final composition is adjusted by the Ca/P ratio. A Ca/P ratio of 1.67 is preferably chosen in order to preferably obtain hydroxyl apatite in the granular material exclusively. If a soluble calcium phosphate (for the in vivo application, the pH value is 7) is to be contained in the granular material, a Ca/P ratio of less than 1.67 is chosen and the soluble β-tricalcium phosphate is formed in the course of the process.

The crystals in the solution tend to agglomerate. If the solid is isolated after precipitation the agglomeration of the crystals, in particular the nanocrystals, is unavoidable (DE 42 32 443 C1). Consequently, granular materials are formed from calcium phosphate crystallites from which the granular material according to the invention, in which crystallites are present in a xerogel matrix, can no longer be obtained.

According to the invention, this problem is solved by homogenising the solution with the precipitated calcium phosphate by stirring and supplying a highly concentrated silicic acid solution, orthosilicic acid being preferably used. Preferably, tetraethyl oxysilane (TEOS) is used which is hydrolysed completely. For this purpose, TEOS and 0.1 molar hydrochloric acid are preferably mixed in a preferred volume ratio of 30:9 with strong stirring until hydrolysis occurs. The water necessary for hydrolysis is provided by the hydrochloric acid solution.

The ratio of calcium phosphate in the precipitated solution and the silicic acid added is selected in such a way that a composition of the granular material according to the invention of approximately 2% by weight to approximately 80% by weight of silica is obtained. It should be noted in particular in this context that 270 g of silica are formed from 1 liter of TEOS. Should a granular material, for example, be obtained which contains 30% by weight of silica, 43 g of silica are required for a solution with 100 g of calcium phosphate which in turn means that approximately 160 ml of TEOS are used. This is independent of how much solvent is contained in the precipitated solution.

According to the invention, the pH of the mixture of precipitated calcium phosphate and silicic acid is adjusted within a range of approximately 2 to approximately 8, preferably in a range of approximately 5 to approximately 6.5.

The silicic acid in the slip begins to condense and the viscosity of the mixture consequently to rise. Up to a viscosity of preferably $2 \cdot 10^5$ cP, sedimentation of calcium phosphates is prevented in the mixture by stirring.

As a result of the beginning gel formation of the silica, the mixture is fixed. The calcium phosphate crystallites are then present in a matrix of silica hydrogel. By removing the solvent, the hydrogel matrix becomes the xerogel matrix according to the invention. Since a granular material according to the invention has a granule grain size of approximately 1 μm to approximately 1000 μm, comminution is necessary. This comminution preferably takes place in the hydrogel state.

The hydrogel is then stored in a closed vessel, preferably at room temperature (if necessary also at temperatures of approximately 60° C. to approximately 80° C.), preferably over a period of approximately 24 h to 48 h. During this period, ageing of the silica gel takes place, i.e. further condensation reactions take place in the solid gel.

Subsequently, the gel with the calcium phosphate is dried in order to remove solvent. The drying temperature is preferably approximately 20° C. to approximately 150° C., preferably drying is carried out at approximately 120° C.

By freezing the moist hydrogel, a granular calcium phosphate/silica material (granular hydroxyl apatite/silica material) is also obtained according to the invention. As a result of the crystallisation of the water, the calcium phosphate and silica of the hydrogel are compressed and granular material is thus formed which can be filtered off after thawing of the ice. The granular material filtered off is preferably dried at approximately 20° C. to approximate 150° C., preferably at approximately 120° C.

A particular embodiment of the production, according to the invention, of the granular material is characterised in that the mixture of precipitated calcium phosphate and silica whose pH is adjusted within a range of approximately 2 to approximately 8, preferably in a range of approximately 5 to approximately 6.5, is spray dried before the gel formation which has the advantage that granule grain sizes in the region according to the invention are obtainable in a simple manner.

Spray drying is a process known in the state of the art (compare e.g. K. Masters, "Spray Drying", $2^{nd}$ ed., John Wiley & Sons, New York, 1976).

During spray drying, liquid products are atomised into fine droplets at the upper end of the drying tower. The droplets are dried while falling freely through a stream of hot air in the tower. The temperature of the stream of hot air is between approximately 80° C. and approximately 200° C. and acts onto the products only for a period of half to one second. After freeze drying, spray drying is the second most gentle industrially used drying method, in particular in the food industry.

If, as a result of the beginning condensation of the silicic acid, a kinematic viscosity of preferably 0.5 to 10 cst is achieved, the mixture is spray dried, the pressure being adjusted to the concentration and the viscosity in such a way that granular materials of 10 μm and smaller are formed (compare in this respect Masters, Spray Drying Handbook, (1979) George Godwin Ltd;).

As a result of the evaporation of the solvent gel formation is achieved and a transition from the wet gel to xerogel initiated. Spray drying has the effect that, as a result of gel formation of the small droplets and drying of the small droplets, granule grains of a corresponding size are formed.

The granular material is characterised in that the calcium phosphate crystallites (preferably HA crystallites) are held together by a porous silica gel.

A characterisation of the granular material is effected by electron microscopy and photocorrelation spectroscopy (E. R. Pike and J. B. Abbiss eds. Light Scattering and Photo Correlation Spectroscopy. Kluwer Academic Publisher, 1997).

A temperature treatment, in the region of approximately 200° C. to approximately 800° C., of the granular material obtainable according to one of the processes described above guarantees that residual solvent is removed from the pores. In this respect, it should be noted that any alcohol present, insofar as it is used as a solvent, is removed as completely as possible before the temperature treatment since it would otherwise subsequently contaminate the product at elevated temperatures by forming carbon.

A temperature treatment at preferably approximately 700° C. to approximately 900° C. (approximately 800° C. in the presence of oxygen (normal air atmosphere)) removes the carbon, which maybe present, by oxidation.

A particular embodiment of the granular material according to the invention contains approximately 0.5 mole % to approximately 35 mole % of a network modifier in the xerogel, preferably $Na_2O$, as described above.

The network modifier is preferably introduced into the finished nanoporous granular material by preferably using an aqueous solution. A drying process at preferably approximately 120° C. to approximately 200° C. subsequently removes the solvent (Example: for 100 g of a granular material with 30% by weight of silica, 8 g of NaOH are dissolved in 50 ml of distilled water. The porous granular material absorbs this solution and it is dried immediately in order to prevent the dissolution of the xerogel in the basic solution). Consequently, the network modifier oxide is present in the granular material in a quantity of 21% by weight, corresponding to 19.3 mole % of $Na_2O$, based on the xerogel.

Consequently, the invention also relates to a process for the production of a granular material according to the invention in which, by using corresponding orthophosphate compounds and calcium compounds (such as e.g. calcium nitrate and ammonium hydrophosphate) as a result of the reaction of the orthophosphate group $PO_4^{3-}$ and calcium ions in aqueous solution, a hydroxyl apatite is precipitated out which, due to the ion concentration fixed in the solution, exhibits a Ca/P ratio of 1.50 to 1.67, a Ca/P ratio of 1.67 being preferably selected if the end product is to subsequently contain hydroxyl apatite as calcium phosphate, and a Ca/P ratio of less than 1.67 being chosen if the soluble β-tricalcium phosphate is to be additionally present in the end product.

The process is, moreover, characterised in that the precipitated hydroxyl apatite is embedded homogeneously in a silicon hydrogel, without forming agglomerates in the aqueous solution, which can be achieved by supplying silicic acid, preferably orthosilicic acid, in particular hydrolysed tetraethyl oxysilane (TEOS) to the aqueous solution and adjusting the pH in such a way that it is in the region of approximately 2 to approximately 8, preferably of approximately 5 to approximately 6.5, such that a gel formation takes place. The quantity of TEOS used is chosen in such a way that the proportion of silica is in the region of approximately 4 to approximately 80% by weight, preferably in the region of approximately 2 to approximately 50% by weight, based on the total mass of the granule grains. As a result of a drying process, a transition from hydrogel to xerogel takes place as a result of which the calcium phosphate crystallites are present in a xerogel matrix.

The granular calcium phosphate material (undissolved calcium phosphate) which is preferably hydroxyl apatite produced according to the invention, if necessary in combination with soluble calcium phosphate, preferably β-calcium phosphate, which contains silica in a defined concentration and morphology, serves as starting product for the production of a highly porous bone substitute material, as has already been mentioned. The production process will be described in further detail below. A use as starting product for plasma spray coating (compare R. B. Heimann, Plasma-Spray Coatings. Principles and Applications, Wiley-VCH Verlag (1998)) of implants. In this case, parts coming in direct contact with the bone, e.g. the shaft of a hip prosthesis is coated with a material. An application in dental implants is also possible.

If the granular material is mixed with bone marrow fluid or with the patient's own blood it should be used as injectable medicine or medicinal product having the purpose of building up osteoporotic bones, of stimulating the build up of the bone in the transition area to the loosened metal implants or of stimulating the healing of parodontal defects.

The highly porous bone substitute material according to the invention is produced from the granular material according to the invention. In this case, a slip is produced from the granular material described and preferably water. Preferably approximately 100 ml to approximately 300 ml of water are added to approximately 100 g of granular material. After adjusting the pH preferably such that it is in the region of approximately 5 to 6.5, the slip is poured into any desired mould and dried. In this way, a highly porous bone substitute material is obtained. The shaped body obtained is comparable to a green body such as it usually arises with ceramic processes (compare in this respect: D. Richerson, Modern Ceramic Engineering, Dekker Publ., J. Reed, Principles of Ceramic Processing, Nanocrystalline Ceramics, M. Winterer, Springer 2002).

Since the calcium phosphate crystallites in the use of the granular calcium phosphate material according to the invention are present in a matrix of silica xerogel, the surface of the granular material obviously consists of silica which, in the pH range chosen, endeavours to effect a condensation reaction between the —SiOH groups of the surfaces of touching granule grains. As a result of the capillary pressure during the drying process, the surfaces of the granule grains are pressed onto each other and bonded by —SiOSi bonds. In this way, the highly porous bone material receives its mechanical stability and the properties according to the invention described above. Silicic acid, in particular orthosilicic acid can be added to the slip as additional binder. According to an embodiment of the invention, TEOS is hydrolysed, for this purpose, with hydrochloric acid and added to the slip. Preferably, 3 ml to 15 ml of TEOS are used per 100 g of granular material.

Preferably, drying of the slip takes place at a temperature of between room temperature and approximately 200° C., particularly preferably between approximately 80° C. and approximately 130° C. After drying, a further temperature treatment takes place in order to solidify the highly porous bone substitute material at a temperature which depends on the presence of network modifiers in the xerogel of the granular material. Without network modifier (pure silica xerogel), the temperature treatment preferably takes place at approximately 700° C. to approximately 900° C., preferably at approximately 800° C. In the presence of a network modifier in the xerogel, the temperature is preferably in the region between approximately 300° C. and approximately 500° C.

As a result of the process described, the highly porous bone substitute material receives its above-described structure and consequently the described properties.

In addition to the nanopores in the xerogel, a category of pores is formed which is determined by the packing of the granule grains and their size. A further pore structure of the order of magnitude of some hundred μm to the mm range, which is to permit the ingrowth of blood vessels, is produced in the shaped body by additionally adding preferably organic powders with a grain size of the pore size desired later on to the shaped body, which are burnt out after the drying process.

Preferably, continuous pores (channels) (of an order of magnitude of some hundred μm to the mm range) are produced by introducing organic fibres of the desired diameter into the slip, which are burnt out after the drying process.

Material suitable for the powder or the fibres is in particular wax since drying of the material which always entails a certain amount of shrinkage can then be carried out at temperatures at which the wax is soft and consequently prevents tearing of the material. An advantageous drying temperature is consequently approximately 40° C. Subsequently, the wax can be removed from the pores by centrifuging at approximately 100° C. Residues of the wax are subsequently burnt out and the carbon formed is removed at approximately 800° C.

The process for the production of the glass ceramics materials according to the invention described is based on the highly porous bone substitute material described.

In this case, the xerogel matrix of the highly porous bone substitute material is converted into a glass matrix without sintering together of the calcium phosphate crystals occurring. This means that the interlinking of the silicon tetrahedra is completed.

A gel-glass transition requires a relatively high temperature of approximately 900° C. to approximately 1200° C. in the case of pure silica. Since the possibility exists at these temperatures that the crystalline calcium phosphate components undergo a phase transition, a highly porous bone substitute material with a network modifier in the xerogel is preferably used. The network modifiers have passed into the highly porous bone substitute material either by the original use of a granular material with a network modifier or the network modifiers are introduced into the finished highly porous bone substitute material by using the same method as for the granular material. In this way, a gel-glass transition takes place at much lower temperatures and the calcium phosphate component does not change. Typical network modifier concentrations are in the region of approximately 0.5 to approximately 35 mole %, preferably approximately 17 to approximately 35 mole %, based on the proportion of silica. A suitable network modifier is $Na_2O$ since the glass phase is thus soluble in body fluids and consequently can also be resorbed.

Since the glass temperature of sodium silicate glass is in the region of approximately 460° C. to approximately 800° C., depending on the sodium content, it is clear that a heat treatment above this temperature range leads to glass very rapidly. If a temperature treatment is carried out approximately 20% to approximately 5% below the glass temperature determined for the composition, the process is slowed down and requires several hours and can be broken off at any time.

During resorption, the glass then goes the opposite way. In other words, the glass turns again into a gel-type structure. The granular calcium phosphate/silica material then provides the possibility of optimising the strength and resorption properties of the bone substitute material according to the invention. An increase in strength will in any case always be accompanied by a decrease in biodegradation.

Many applications are possible for the bone substitute material according to the invention. For small defects such as those partially occurring in surgery on the jaw bone, a granular material of the highly porous bone substitute material can be used for filling. In the case of greater defects where the remaining bone still sufficiently stabilises the form of the defect, shaped bodies of the highly porous bone substitute material must be used.

Shaped bodies consisting of a combination of mechanically relatively strong bone substitute materials (the matrix consists of glass) and the highly porous bone substitute materials (the matrix consists of xerogel), in particular, have an interesting application in particular in the case of larger defects or also defects in the case of which no native bone has remained as guiding rail.

According to the invention, these shaped bodies possess, at least on one side, a layer of the inorganic resorbable bone substitute material with glass as matrix (increased strength) and in this layer holes of an order of magnitude of 0.5 to 5 millimeters are present and these holes take up a proportion of the volume in the layer of 5 to 80%. The entire volume, including the holes in the more solid material, is taken up by the material which has a xerogel as matrix. The hole structure in the solid layer is to allow an ingrowth of blood vessels.

Consequently, the invention also relates to the use of the granular materials and bone substitute materials according to the invention for the production of shaped bodies, preferably a cube, a plate, a hollow cylinder or a wedge.

Moreover, the invention permits the use of the above-mentioned granular silica/calcium phosphate material for coating implants (compare above). Particularly preferably, the coating is effected by plasma spray coating.

Moreover, the invention relates to the use of a granular material according to the invention for the production of a medicine or medical product for building up osteoporotic bones, for stimulating the bone build up in the transition area to loosened metal implants or for stimulating healing of parodontal defects. For this purpose, the granular material is preferably mixed with bone marrow fluid or blood.

The subject matter of the invention moreover consists of a medicine or medical product which comprises a granular material according to the invention which is mixed with bone marrow fluid or blood of the patient (consequently autologous).

The subject matter of the invention moreover consists of a medicine or medical product which comprises a highly porous bone substitute material according to the invention or a glass ceramic material as bone substitute material, the bone substitute material being brought into contact with the bone marrow fluid or blood of the patient (consequently autologous) directly before implantation such that the pores of the materials are completely filled.

The present invention will be explained in further detail in the following examples and figures without being restricted thereto.

EXAMPLES

Example 1

Production of Granular Calcium Phosphate Material

Figure 4:
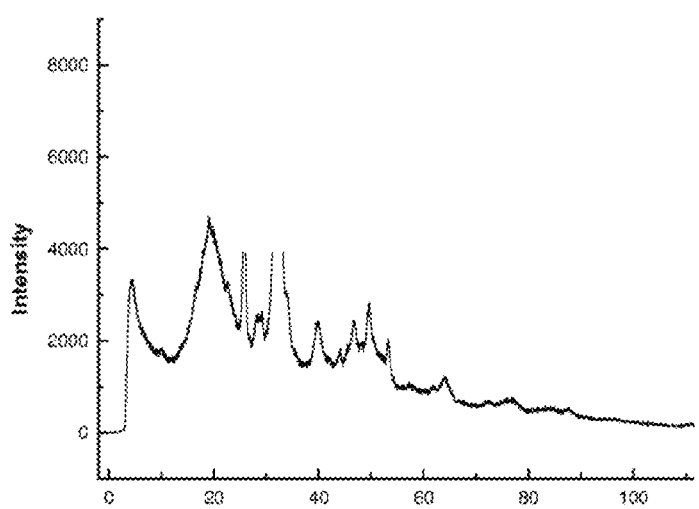
FIG. 4 shows a granular calcium phosphate material according to an aspect of the present disclosure.

A solution of 3 mmole/m$^3$ of $Ca(H_2PO_4)_2$ and a solution of 7 mmole/m$^3$ of $CaCl_2$ are stirred together (giving a Ca/P ratio of 1.67) and a pH of 7 is adjusted with NH4OH. The precipitated material is measured by powder diffractometry. FIG. 4 shows the result. It is a pure phase hydroxyl apatite which does not change even during the subsequent process steps.

The solution with the precipitated hydroxyl apatite is prevented from settling out by continuous stirring and concentrated until 50 g of hydroxyl apatite remains per 100 ml of solvent. 60 ml of tetraethyl oxysilane (TEOS) and 18 ml of 0.05 molar hydrochloric acid are vigorously stirred until the hydrolysis of the TEOS has been completed requiring a period of approximately 15 minutes and detectable by a temperature increase from room temperature to approximately 50° C.

This solution is passed to the solution with the precipitated homogenously distributed hydroxyl apatite and the pH is adjusted to approximately 6.0 with $NH_4OH$. This mixture is stirred until a viscosity of approximately 2*10^5 cP is reached (as a result of the beginning gel formation of the silica, the solution becomes paste-like). Following the gel formation which sets in immediately, the preparation is stored for 24 hours in a closed vessel and subsequently granulated.

Subsequently, drying takes place at 80° C. for a period of 2 hours. During this process, the transition from hydrogel to xerogel takes place.

The granular material is rinsed in distilled water and subsequently dried again. For this purpose, a temperature treatment of 120° C. was chosen for a period of two hours.

The subsequent temperature treatment at 800° C. requires a period of 1 hour. The granular material formed consists of calcium phosphate to an amount of 75% by weight and of silica to an amount of 25% by weight.

Figure 5:
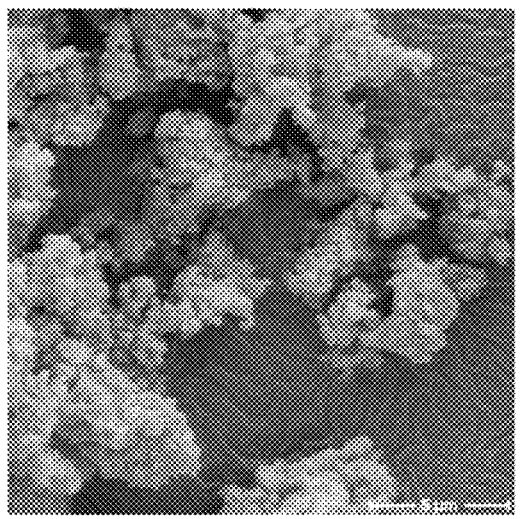
FIG. 5 shows scanning electron micrographs of a granular material according to an aspect of the present disclosure.

The granular material formed is characterised by scanning electron micrographs as shown in FIG. 5. Granule grains within the order of magnitude of 1 µm to 5 µm can be recognised.

Figure 6:
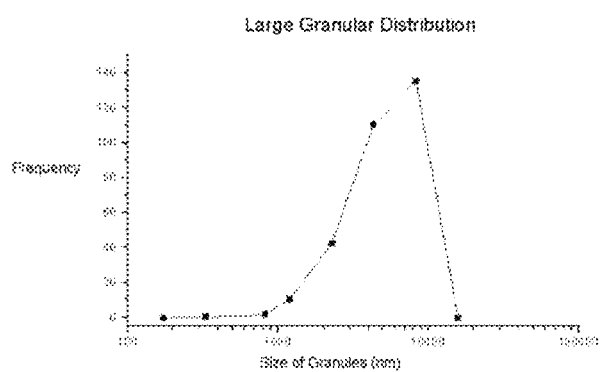
FIG. 6 shows dynamic light scattering of a granular material according to an aspect of the present disclosure.

From the granular material, a slip is produced with water and the size distribution of the granule grains is determined by dynamic light scattering (E. R. Pike and J. B. Abbiss eds. Light Scattering and Photo Correlation Spectroscopy. Kluwer Academic Publisher, 1997). The result is shown in FIG. 6.

Figure 7:
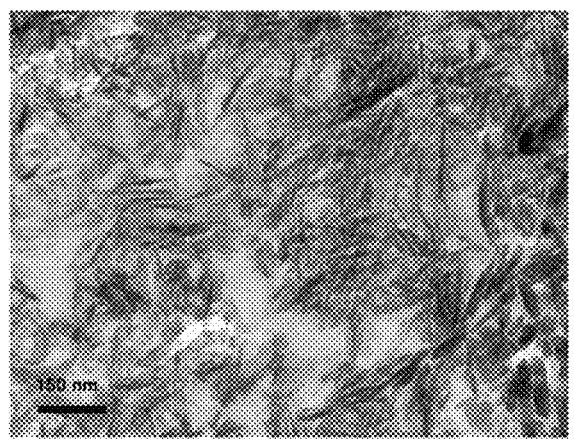
FIGS. 7 and 8 show transmission electron micrographs of cross sections through granule grains of a granular material according to an aspect of the present disclosure.
Figure 8:
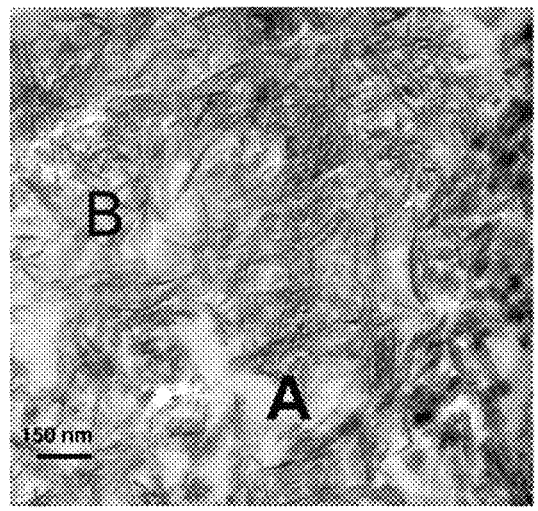

FIGS. 7 and 8 show transmission electron micrographs of cross sections through the granule grains. For this purpose, the material was embedded in epoxide and sections approximately 60 nm thick were prepared. The crystallites are platelets with an average platelet diameter of approximately 150 nm and a platelet thickness of approximately 10-20 nm. It can be seen very clearly how the crystallites are embedded in the xerogel matrix even though the contrast between the epoxide (embedding material) and the silica xerogel is relatively weak. In FIG. 7, region A, for example, is a pore filled with epoxide and region B is a typical area in which the hydrogel apatite is embedded in xerogel.

Example 2

Production of Granular Calcium Phosphate Material

An aqueous solution of calcium nitrate and ammonium hydrophosphate with a ratio of calcium to phosphate of 1.67 is homogeneously mixed with a magnetic stirrer and a pH of 10 is adjusted by means of $NH_4OH$. The precipitated material is washed four times with distilled water and centrifuged and subsequently dispersed in ethanol.

Based on a proportion of solids of 72.9 g HA, 30 ml of TEOS are mixed with 9 ml of an 0.1 mole/l HCl solution and 9 ml of ethanol. Following the hydrolysis of the TEOS, this mixture is introduced into the HA slip and distributed homogeneously and a pH of 6.0 is adjusted.

Spray drying is carried out by pressing the homogenised slip with compressed air at a pressure of between 50 and 100 kPa through a nozzle and rapid drying takes place in a coaxial stream of air at a temperature of 100° C.

The subsequent temperature treatment at 800° C. requires a time of 1 hour.

The granular material formed differs regarding the properties from the granular material above all by the size of the granule grains which has a considerably narrower distribution and a maximum with a diameter of 18 μm.

Example 3

Production of Granular Calcium Phosphate

An aqueous solution of 0.3 M orthophosphoric acid ($H_3PO_4$) is mixed with an aqueous suspension of 0.1 M calcium hydroxide ($Ca(OH)_2$) at room temperature. In this way, a Ca/P ratio of 1.5 is obtained. A pH of 10 is adjusted with $Na_4OH$. The precipitated material is washed four times with distilled water and centrifuged and subsequently dispersed in water such that 50 g of calcium phosphate remain per 100 ml of solvent. 30 ml of TEOS and 9 ml of 0.05 molar hydrochloric acid are vigorously stirred until the hydrolysis of the TEOS has been completed, requiring a time of approximately 15 minutes and detectable by a temperature increase from room temperature to approximately 50° C.

This solution is passed to the solution with the precipitated, homogeneously distributed hydroxyl apatite and the pH is adjusted to approximately 6.0 with $Na_4OH$. This mixture is stirred further until a viscosity of approximately $2 \cdot 10^5$ cP is reached (as a result of the gel formation of the silica setting in, the solution becomes paste-like). Following the gel formation which sets in immediately, the preparation is stored for 24 hours in a closed vessel, subsequently granulated.

Subsequently, drying takes place at 80° C. over a period of 2 hours. During this process, the transition from hydrogel to xerogel takes place.

The granular material is rinsed in distilled water and subsequently dried again. For this purpose, a temperature treatment of 120° C. is chosen for a period of two hours.

The subsequent temperature treatment at 800° C. requires a time of 1 hour. The granular material formed consists of calcium phosphate to an amount of 86% by weight and of silica to an amount of 14% by weight.

Figure 9:
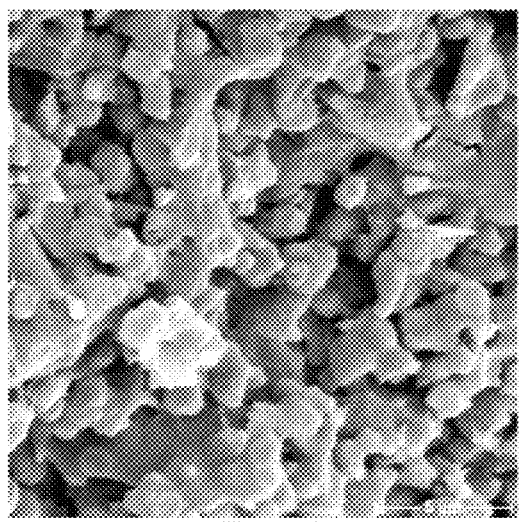
FIGS. 9 and 10 show scanning electron micrographs of a granule grain according to an aspect of the present disclosure.
Figure 10:
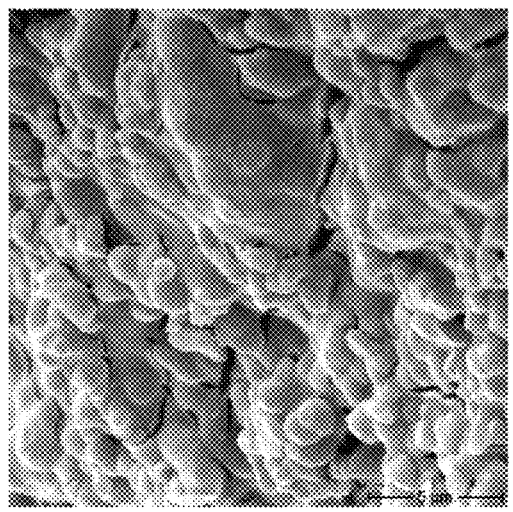

FIGS. 9 and 10 show scanning electron micrographs of a granule grain. In FIG. 9, the interior of a ground granule grain along a fracture line is visible. FIG. 10 shows the surface of a granule grain. In this example, relatively large crystallites with a diameter of approximately 1 μm are present in the form of β-tricalcium phosphate. In the micrographs, the xerogel appears as a compact material which is obviously attributable to the resolution of the scanning micrographs which do not completely resolve the porosity of the xerogel. However, it can been seen fairly clearly how the xerogel forms a matrix in which the crystallites are embedded and that entire granule grain is surrounded by a xerogel layer.

Example 4

Production of the Highly Porous Bone Substitute Material 100 g of the granular material, the production of which is described in example 1 and which contains 25% by weight of silica is mixed by stirring with 150 ml of distilled water and poured into moulds of 8 mm·15 mm·30 mm respectively.

Drying takes place at 80° C. for 3 hours. During the subsequent temperature treatment, the samples are maintained at 120° C. for 2 hours and, subsequently, the temperature is increased to 800° C. and held for 1 hour.

The bone substitute material has a porosity of approximately 60%.

Figure 11:
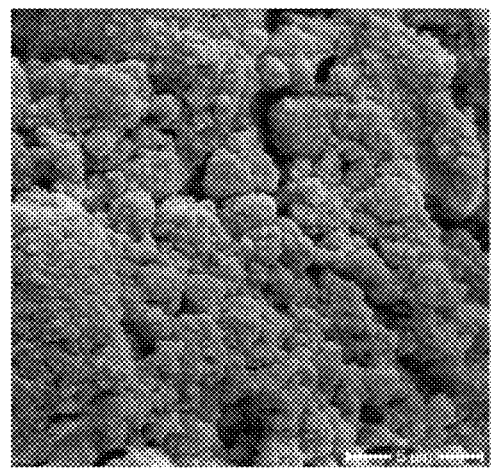
FIG. 11 shows the scanning electron micrograph of a material according to an aspect of the present disclosure.

FIG. 11 shows the scanning electron micrograph of the material. The granule grains whose original shape can be seen in FIG. 5 now form a continuous 3-dimensional structure with pores in the micrometer range.

The nanostructure in the interior of the granules remains unchanged.

Example 5

Production of the Highly Porous Bone Substitute Material 142 ml of water are mixed with 8 ml of hydrolysed TEOS solution. For the hydrolysis, 18 ml of 0.05 molar hydrochloric acid are added to 30 ml of TEOS and stirred until the hydrolysis is completed which can be seen by a temperature increase from room temperature to approximately 50° C.

100 g of granular material whose production is described in example 1 are homogeneously distributed in this solution. A further treatment follows as in example 4.

By additionally introducing the silica, the essential structure of the material (micrometer pores and nanometapores) is not altered. The granular materials are firmly bonded which increases the overall strength of the highly porous bone substitute material by approximately 50%.

Example 6

Production of the Highly Porous Bone Substitute Material But with Macropores

Wax threads with a diameter of 0.2 mm are introduced into moulds of example 4 in a completely random manner such that they represent a volume fraction of 30% of the mould content. A slip of silica-containing granular calcium phosphate material as described in example 5 is introduced into these moulds. Drying now takes place at 40° C. since the wax threads are soft in this case and not yet liquid and are consequently not distributed in the micrometer pores being formed, over a period of 4 hours.

During a temperature treatment at 800° C. over a period of 1 hour, the wax is burnt out.

The macropores which have been formed instead of the wax threads take up approximately 30 vol % such that an overall porosity of 72% has been formed since the micrometer and nanometer structure has not changed in comparison with example 5 or 6.

Example 7

Production of a Glass Ceramic Material

The starting point for the production of the glass ceramic material as bone substitute material is the highly porous bone substitute material produced in example 4.

A shaped body of this material has a density of 0.8 g/cm$^3$ and consequently a porosity of approximately 60%. A volume of 1000 ml of the shaped body contains 200 g of silica. In order to introduce the network modifier into the xerogel of the shaped body with the volume of 1000 ml, 50 g of NaOH are dissolved in 600 ml of water and introduced into the pores of the shaped body. The shaped body absorbs the solution completely and drying at 120° C. takes place. Consequently, the network modifier oxide is present in the shaped body in a quantity of 20% by weight corresponding to approximately 19 mole % of Na$_2$O, based on the xerogel.

Then follows a temperature treatment at 650° C. for two hours. As a result, the xerogel passes into the state of glass. Sodium silicate glass is formed. The shaped body shrinks and retains a residual porosity of approximately 30%.

Figure 12:
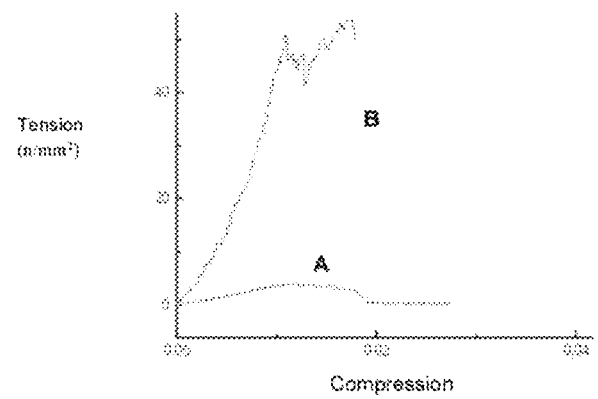
FIG. 12 is a graph showing the mechanical strength of bone substitute material according to an aspect of the present disclosure.

FIG. 12 documents the mechanical strength of the bone substitute materials. Curve A in the stress-compressive strain diagram shows the material with silicon xerogel as matrix. It is a material with 24 percent by weight of silica and with hydroxyl apatite as crystalline component.

Curve B in the diagram represents a material of identical composition, the xerogel matrix having been converted into a glass. The rupture strength has risen from approximately 3 to 50 MPa.

Example 7

In Vivo Testing of the Highly Porous Bone Substitute Material

Göttinger mini-pigs were used for the animal experiments in order to test the properties of the material as bone substitute. The animals were adult (1 year old) and weighed between 25 and 30 kg. The bone defects exceeded the critical size of 5 cm$^3$; their dimensions are approximately 3.0 cm·1.5 cm·1.5 cm. They were implanted in the lower jaw, completely filled with the bone substitute material and closed with the bone skin. After 8 months, the pigs were killed and the lower jaws removed and x-ray, histological and scanning microscopic investigations were carried out.

Figure 13:
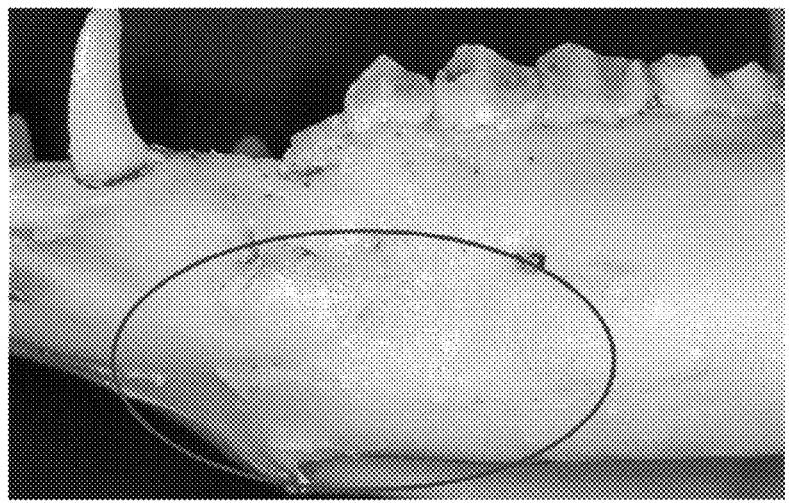
FIG. 13 shows a lower jaw with a previous defect which has been filled with a material according to an aspect of the present disclosure.

FIG. 13 shows the lower jaw with the previous defect which had been filled with the material of the example, 8 months after the operation. The defective area has completely healed clinically. Histological investigations show that less than 1% of the biomaterial, taken as the mean value of several test animals, is present in the defective area.

Figure 14:
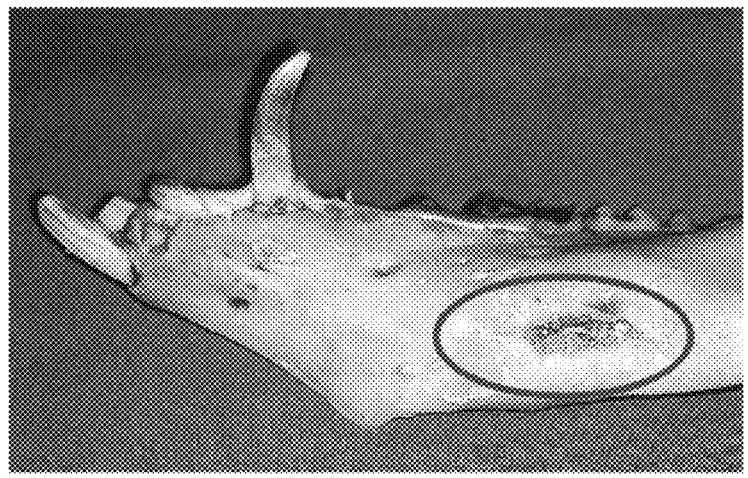
FIG. 14 shows a lower jaw with a void defect.

FIG. 14 shows a comparative study with a void defect. This defect is encapsulated by connective tissue and has not healed.

Figure 15:
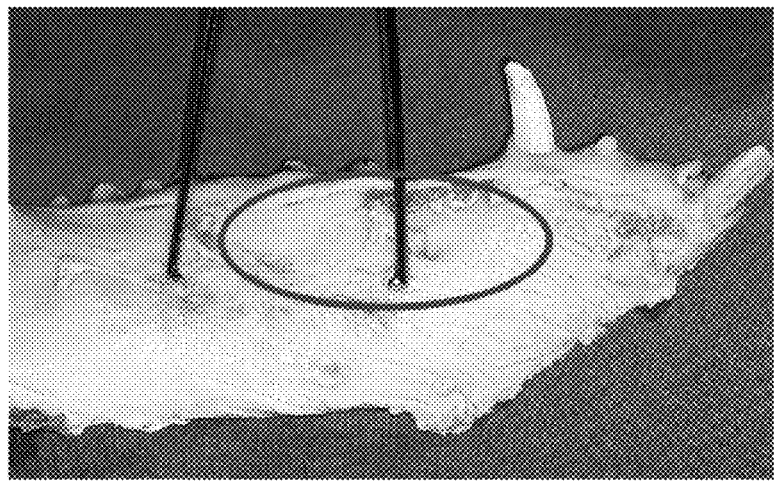
FIG. 15 shows a comparative study of a lower jaw with a commercial bone substitute material based on hydroxyl apatite.

FIG. 15 shows a comparative study with a commercial bone substitute material based on hydroxyl apatite. Although the defect has healed, the biomaterial has not been degraded and remains in the bone as a foreign body.

Figure 16:
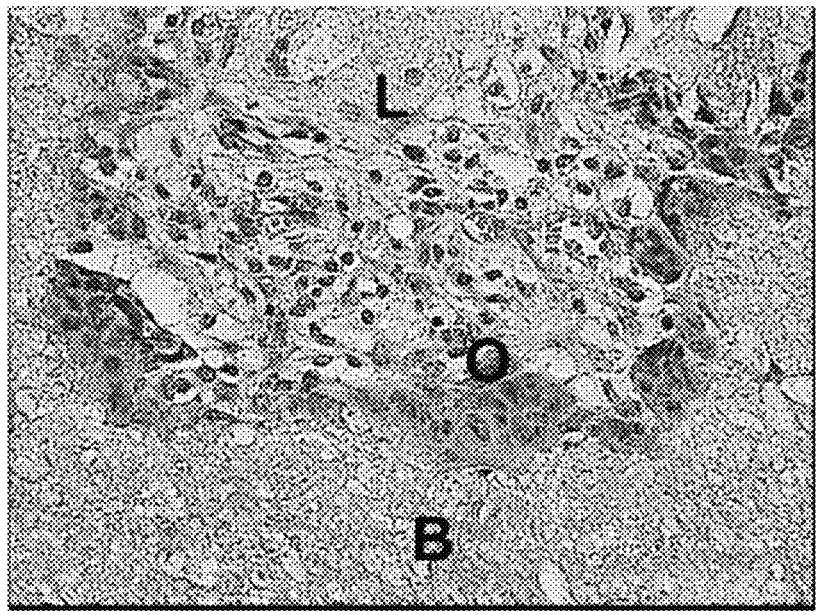
FIG. 16 shows a light micrograph of a histological section of a material according to an aspect of the present disclosure.

FIG. 16 shows a light micrograph of a histological section. It involves a demineralised histological section with hemalum stain. A laguna (L) discernible in the biomaterial of example (B). At the bottom of the laguna, osteoclasts (O) are seen decomposing biomaterial. This means that the biodegradation of the material takes place via osteoclasts which is of decisive importance for an application.

Example 8

Figure 17:
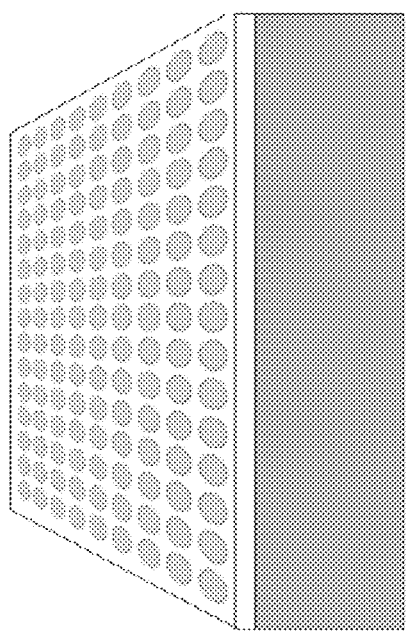
FIGS. 17 and 18 show shaped bodies which combine the properties of two materials according to an aspect of the present disclosure with different mechanical properties.
Figure 18:
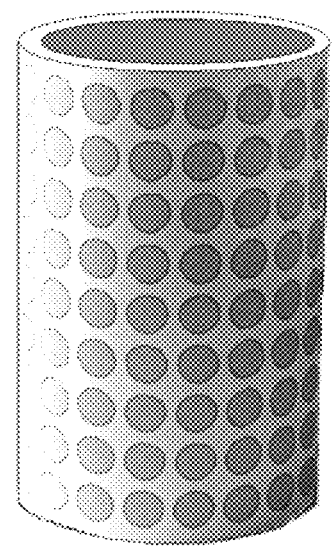

In FIG. 17, a shaped body is shown which combines the properties of the two materials with different mechanical properties and is intended for major bone defects. The material with the glass as matrix forms a support layer on one side which has a thickness of the order of magnitude of two mm, which is again provided with a system of holes. The volume of the shaped body and the holes in the stable layer are filled by the material with xerogel as matrix since this material has the better bioactive properties. FIG. 18 shows a further possible shaped body. The cylinder has a jacket of the material with the glass as matrix. This jacket also possesses a system of holes, which like the entire volume, are filled with the material with xerogel as matrix.

The invention claimed is:

1. A material having granular grains comprising individual crystallites of hydroxyl apatite embedded into and enclosed by a silica xerogel matrix, wherein said individual crystallites of hydroxyl apatite have a size of approximately 10 nm to approximately 2000 nm, and are homogeneously distributed in the matrix, said granule grains have a size of approximately 1μm to approximately 1000 μm, and the silica is approximately 2 to approximately 80% by weight of the total mass of said granule grains.

2. The material according to claim 1, wherein said xerogel matrix further comprises pores having an average diameter in the region of 0.5 nm to 20 nm.

3. The material according to claim 1, wherein said granule grains further comprise pores that amount to approximately 10 volume % to approximately 60 volume %, based on the volume of the granule grains.

4. The material according to claim 1, wherein said individual crystallites of hydroxyl apatite have an average diameter of between 10 nm to 200 nm.

5. The material according to claim 1, wherein said material further comprises soluble calcium phosphate.

6. The material according to claim 5, wherein said soluble calcium phosphate is present in a proportion of approximately 5% by weight to 50% by weight, based on the total proportion of calcium phosphate.

7. The material according to claim 5, wherein said soluble calcium phosphate is β-tricalcium phosphate.

8. The material according to claim 1, further comprising a network modifier oxide.

9. The material according to claim 8, wherein said network modifier oxide is present in a proportion of approximately 0.5 to approximately 35 mole %, based on the silica.

10. The material according to claim 9, wherein said network modifier oxide is Na$_2$O.

11. A highly porous bone substitute material comprising granule grains of the material according to claim 1, wherein said granule grains form a three-dimensional structure and said highly porous bone substitute material exhibits pores that are approximately the size of the granule grains, and said granule grains comprise individual crystallites of hydroxyl apatite embedded into and enclosed by a silica xerogel matrix, wherein said individual crystallites of hydroxyl apatite have a size of approximately 10 nm to approximately 2000 nm, and are homogeneously distributed in the matrix, said granule grains have a size of approximately 1 μm to approximately 1000 μm, and the silica is approximately 2 to approximately 80% by weight of the total mass of said granule grains.

12. The highly porous bone substitute material according to claim 11, wherein said highly porous bone substitute material exhibits interconnecting macropores in the region of approximately 100 μm to several 1000 μm.

13. The highly porous bone substitute material according to claim 11, wherein said highly porous bone substitute material exhibits a total porosity of approximately 30 to approximately 90 volume %.

14. The highly porous bone substitute material according to claim 11, wherein said highly porous bone substitute material exhibits a fracture strength of approximately 0.1 megapascals (MPa) to 15 MPa.

15. The highly porous bone substitute material according to claim 11, further comprising a network modifier oxide.

16. The highly porous bone substitute material according to claim 15, wherein said network modifier oxide is present in a proportion of approximately 0.5 to approximately 35 mole %, based on the silica.

17. The highly porous bone substitute material according to claim 15, wherein said network modifier oxide is $Na_2O$.

18. The highly porous bone substitute material according to claim 11, wherein said material is a shaped body.

19. The highly porous bone substitute material according to claim 18, wherein said shaped body is selected from the group consisting of a cube, a plate, a hollow cylinder, or a wedge.

20. A method of producing a shaped body using the material according to claim 1, comprising forming a material into a shaped body wherein said material is a highly porous bone substitute material comprising granular grains of approximately 1 μm to approximately 1000 μm having individual crystallites of hydroxyl apatite of approximately 10 mn to approximately 2000 nm embedded into, enclosed by, and homogeneously distributed in a silica xerogel matrix and said silica is approximately 2 to approximately 80% by weight of the total mass of said granule grains.

21. The method according to claim 20, wherein said shaped body is selected from the group consisting of a cube, a plate, a hollow cylinder, and a wedge.

22. A method of coating an implant using the material according to claim 1, comprising coating an implant with a material comprising granular grains having a size of approximately 1 μm to approximately 1000 μm and having individual crystallites of hydroxyl apatite of approximately 10 nm to approximately 2000 nm embedded into, enclosed by, and homogeneously distributed in a silica xerogel matrix and said silica is approximately 2 to approximately 80% by weight of the total mass of said granule grains.

23. The method according to claim 22, wherein said implant coating is a plasma spray coating.

24. A method of stimulating healing of periodontal defects in a patient comprising mixing bone marrow fluid, the blood of said patient, or saline with a material having granular grains having a size of approximately 1 μm to approximately 1000 μm comprising individual crystallites of hydroxyl apatite having a size of approximately 10 nm to approximately 2000 nm embedded into, enclosed by, and homogeneously distributed in a silica xerogel matrix, wherein the proportion of said silica is approximately 2 to approximately 80% by weight based on the total mass of said granule grains, and implanting the mixture in said patient in need of healing of periodontal defects.

25. A method of building up osteoporotic bone in a patient, comprising mixing bone marrow fluid, the blood of said patient, or saline with a material having granular grains comprising individual crystallites of hydroxyl apatite having a size of approximately 10 nm to approximately 2000 nm embedded into, enclosed by, and homogeneously distributed in a silica xerogel matrix, wherein said individual crystallites of hydroxyl apatite have a size of approximately 10 nm to approximately 2000 nm, said individual crystallites are homogeneously distributed in the matrix, said granule grains have a size of approximately 1 μm to approximately 1000 μm, and wherein the proportion of said silica is approximately 2 to approximately 80% by weight based on the total mass of said granule grains and implanting said mixture in said patient in need of building up osteoporotic bone.

26. A medicine or medical product comprising granular grains of individual crystallites of hydroxyl apatite embedded into and enclosed by a silica xerogel matrix, wherein said individual crystallites of hydroxyl apatite have a size of approximately 10 nm to approximately 2000 nm, said individual crystallites are homogeneously distributed in the matrix, said granule grains have a size of approximately 1 μm to approximately 1000 μm, the proportion of said silica is approximately 2 to approximately 80% by weight based on the total mass of said granule grains, and wherein said individual crystallites of hydroxyl apatite embedded into and enclosed by a silica xerogel matrix is mixed with bone marrow fluid or blood from a patient.

27. A method of producing hydroxyl apatite embedded into and enclosed by a silica xerogel matrix comprising:
   a) precipitating hydroxyl apatite out of an aqueous solution wherein said apatite has a Calcium/Phosphate ratio of 1.50 to 1.67;
   b) forming crystallites of approximately 10 nm to approximately 2000 nm and granule grains of a size of approximately 1 μm to approximately 1000 μm;
   c) forming a gel that has the individual crystallites of precipitated hydroxyl apatite homogenously embedded into a silicon hydrogel without agglomerates in said aqueous solution;
   d) forming a granulated hydrogel and subsequently; and
   e) subjecting said hydrogel to a drying process such that individual calcium phosphate crystallites are homogenously distributed in a xerogel matrix,
   wherein said hydroxyl apatite embedded into and enclosed by said xerogel matrix comprises granular grains of approximately 1 μm to approximately 1000 μm having individual crystallites of hydroxyl apatite of approximately 10 nm to approximately 2000 nm embedded into, enclosed by, and homogeneously distributed in a silica xerogel matrix and said silica is approximately 2 to approximately 80% by weight of the total mass of said granule grains.

28. The method of producing individual hydroxyl apatite crystallites embedded into and enclosed by a silica xerogel matrix granular material according to claim 27, wherein said hydrogel is stored in a closed vessel at room temperature.

29. The method of producing individual hydroxyl apatite crystallites embedded into and enclosed by a silica xerogel matrix granular material according to claim 27, wherein the drying of said hydrogel is carried out at a temperature of approximately 20° C. to approximately 150° C.

30. A method of producing a material having granular grains comprising individual crystallites of crystalline hydroxyl apatite embedded into and enclosed by a silica xerogel matrix, comprising:
   a) precipitating hydroxyl apatite out of an aqueous solution wherein said apatite has a Calcium/Phosphate ratio of 1.50 to 1.67;
   b) forming individual crystallites of approximately 10 nm to approximately 2000 nm and granule grains of a size of approximately 1 μm to approximately 1000 μm;

c) forming a gel that has the precipitated individual crystallites of hydroxyl apatite homogenously embedded into a silicon hydrogel without agglomerates in said aqueous solution; and d) spray drying said aqueous solution before gel formation, wherein said material having granular grains comprising individual crystallites of crystalline hydroxyl apatite embedded into and enclosed by a silica xerogel matrix comprises granular grains of approximately 1 μm to approximately 1000 μm having individual crystallites of hydroxyl apatite of approximately 10 nm to approximately 2000 nm embedded into, enclosed by, and homogeneously distributed in a silica xerogel matrix and said silica is approximately 2 to approximately 80% by weight of the total mass of said granule grain.

31. A method of producing granule grains of individual hydroxyl apatite crystallites embedded into and enclosed by a silica xerogel matrix, comprising:

a) precipitating hydroxyl apatite out of an aqueous solution wherein said apatite has a Calcium/Phosphate ratio of 1.50 to 1.67;

b) forming individual crystallites of approximately 10 nm to approximately 2000 nm and granule grains of a size of approximately 1 μm to approximately 1000 μm;

c) forming a gel that has the precipitated individual crystallites of hydroxyl apatite homogenously embedded into a silicon hydrogel without agglomerates in said aqueous solution;

d) cooling said hydrogel to temperatures below the freezing point of the solvent; and e) filtering the granular silica material and hydroxyl apatite after said hydrogel is thawed, wherein said granule grains of individual hydroxyl apatite crystallites embedded into and enclosed by a silica xerogel matrix comprises granular grains of approximately 1 μm to approximately 1000 μm having individual crystallites of hydroxyl apatite of approximately 10 nm to approximately 2000 nm embedded into, enclosed by, and homogeneously distributed in a silica xerogel matrix and said silica is approximately 2 to approximately 80% by weight of the total mass of said granule grains.

32. The method according to claim 27, wherein said aqueous solution comprises calcium nitrate and ammonium hydrophosphate with a Calcium/Phosphate ratio of 1.67.

33. The method according to claim 27, wherein said aqueous solution comprises calcium nitrate and ammonium hydrophosphate with a Calcium/Phosphate ratio equal to or more than 1.5 and less than 1.67 and the granular material further comprises soluble β-tricalcium phosphate.

34. The method according to claim 27, wherein said aqueous solution further comprises hydrolysed tetraethyl oxysilane.

35. The method according to claim 27, wherein said granular grains are 10 μm or less.

36. The method according to claim 35, wherein said gel has a kinematic viscosity of 0.5 to 50 centiStokes (cSt).

37. A method of producing the highly porous bone substitute material of claim 11, comprising:

a) precipitating hydroxyl apatite out of an aqueous solution wherein said apatite has a Calcium/Phosphate ratio of 1.50 to 1.67;

b) forming individual crystallites of approximately 10 nm to approximately 2000 nm and granule grains of a size of approximately 1 μm to approximately 1000 μm;

c) forming a gel that has the precipitated individual crystallites of hydroxyl apatite homogenously embedded into a silicon hydrogel without agglomerates in said aqueous solution;

d) forming a granulated hydrogel;

e) subjecting said hydrogel to a drying process such that individual hydroxyl apatite crystallites are embedded in a xerogel matrix and a granule material is formed;

f) stirring said granular material with water to form a slip;

g) adjusting the pH of said slip to between approximately 2 and approximately 8;

h) pouring said slip into a mold; and i) drying said mold.

38. The method according to claim 37, further comprising adding silicic acid to said slip.

39. The method according to claim 38, wherein said silicic acid is hydrolysed tetraethyl oxysilane.

40. The method according to claim 37, further comprising producing pore structures by adding organic powder to said slip.

41. The method according to claim 37, further comprising producing continuous pore structures having a size of 100 μm to the millimeter range by adding organic fibers to said slip.

42. The method according to claim 40, wherein said organic powder comprises wax.

43. The method according to claim 42, further comprising drying said material at approximately 40° C., burning the wax residue, and removing the carbon formed during the burning.

44. The method according to claim 37, wherein a solution comprising a network modifier oxide is introduced into said pores of said bone substitute material such that said network modifier oxide is present in a proportion of approximately 0.5 to approximately 35 mole %, based on the silica.

45. The method according to claim 37, wherein said mould is a cylinder with an average diameter of approximately 0.4 to approximately 2 mm and a length of approximately 1 to approximately 6 mm.

46. A medicine or medical product comprising the bone substitute material of claim 11, wherein said bone substitute material comprises pores that are filled with bone marrow fluid or blood of a patient in need of treatment.

47. A method of stimulating bone build up in a patient, comprising:

mixing bone marrow fluid of said patient, blood of said patient, or saline with a material according to claim 1, said material having granular grains comprising individual crystallites of hydroxyl apatite embedded into and enclosed by a silica xerogel matrix, wherein said individual crystallites of hydroxyl apatite have a size of approximately 10 nm to approximately 2000 nm, said individual crystallites are homogeneously distributed in the matrix, said granule grains have a size of approximately 1 μm to approximately 1000 μm, and the proportion of said silica is approximately 2 to approximately 80% by weight based on the total mass of said granule grains; and implanting the mixture in a patient in need of said treatment.

48. The method of claim 47, wherein said implanting is at a transition area of a loosened metal implant in said patient.

49. The method according to claim 22, wherein said implant is selected from the group consisting of a metal implant, a dental implant, and a shaft of a hip prosthesis.

* * * * *

UNITED STATES PATENT AND TRADEMARK OFFICE
CERTIFICATE OF CORRECTION

PATENT NO. : 8,715,744 B2  
APPLICATION NO. : 10/557796  
DATED : May 6, 2014  
INVENTOR(S) : Thomas Gerber Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1211 days.

Signed and Sealed this

Twenty-ninth Day of September, 2015

Michelle K. Lee
*Director of the United States Patent and Trademark Office*